United States Patent [19]

Wu et al.

[11] Patent Number: 5,705,387
[45] Date of Patent: Jan. 6, 1998

[54] HEAT-INDUCIBLE N-DEGRON MODULE

[75] Inventors: Peipei Wu, Marblehead, Mass.; Jürgen Dohmen; Alexander Varshavsky, both of Pasadena, Calif.

[73] Assignee: California Institute of Technology, Pasadena, Calif.

[21] Appl. No.: 637,508

[22] Filed: Apr. 25, 1996

Related U.S. Application Data

[62] Division of Ser. No. 192,479, Feb. 4, 1994, Pat. No. 5,538,862.

[51] Int. Cl.[6] .................. C12N 5/10; C12P 21/02; C07K 14/47
[52] U.S. Cl. .................... 435/325; 435/69.7; 530/350
[58] Field of Search ................... 435/69.7, 69.1, 435/325, 254.11; 530/350

[56] References Cited

U.S. PATENT DOCUMENTS

| | | | |
|---|---|---|---|
| 5,093,242 | 3/1992 | Bachmair et al. | 435/69.7 |
| 5,122,463 | 6/1992 | Varshavsky et al. | 435/172.3 |
| 5,132,213 | 7/1992 | Bachmair et al. | 435/69.7 |
| 5,196,321 | 3/1993 | Bachmair et al. | 435/69.7 |
| 5,212,058 | 5/1993 | Baker et al. | 435/252.33 |

OTHER PUBLICATIONS

Park, E-C., et al., "A strategy for the generation of conditional mutations by protein destabilization", *Proc. Natl. Acad. Sci. USA* 89: 1249 (1992).

Varshavsky, A., "The N-End Rule", *Cell* 69: 725 (1992).

Pringle, J.R., "Induction, Selection, and Experimental Uses of Temperature-Sensitive and Other Conditional Mutants of Yeast", in *Methods in Cell Biology* 12, : (Prescott ed. ): 233, Academic Press, New York (1975).

*Primary Examiner*—Robert A. Wax
*Assistant Examiner*—Kawai Lau
*Attorney, Agent, or Firm*—Kevin M. Farrell

[57] ABSTRACT

The N-degron is an intracellular degradation signal whose essential determinant is a specific, destabilizing, N-terminal amino acid residue. A set of N-degrons containing different destabilizing residues is manifested as the N-end rule, which relates the in vivo half-life of a protein to the identity of its N-terminal amino acid residue. Disclosed herein is a heat-inducible N-degron module. A heat-inducible N-degron module is a protein or peptide bearing a destabilizing N-terminal amino acid residue which becomes a substrate of the N-end rule pathway only at a temperature high enough to result in at least partial unfolding of the protein. At this elevated (nonpermissive) temperature, the heat-inducible N-degron module (and any protein or peptide attached at its C-terminus) is rapidly degraded in a cell in which the N-end rule pathway is operative. Also disclosed are DNA and protein fusion constructs, methods for screening for additional heat-inducible N-degron modules and methods for using the disclosed heat-inducible N-degron modules.

9 Claims, 1 Drawing Sheet

| domain 1 | domain 2 | domain 3 |
|---|---|---|
| Ubiquitin | DHFR[ts] | protein of interest |

| t (°C) | Half-life in S. cerevisiae | | Phenotypes with Ura3 as domain 3 | | Phenotypes with Cdc28 as domain 3 | |
|---|---|---|---|---|---|---|
| | UBR1 | ubr1Δ | UBR1 | ubr1Δ | UBR1 | ubr1Δ |
| 23°C | deubiquitination (cotranslational) | | | | | |
| 23°C | long | long | Ura[+] | Ura[+] | growth | growth |
| 37°C | short | long | Ura[−] | Ura[+] | arrest | growth |

HEAT-INDUCIBLE N-DEGRON MODULE

This application is a division of application Ser. No. 08/192,479, filed Feb. 4, 1994, now U.S. Pat. No. 5,530,862.

GOVERNMENT SUPPORT

Experimental work disclosed herein was supported by a grant from the National Institutes of Health and the government has certain rights in the invention.

BACKGROUND OF THE INVENTION

A conditional mutant retains the function of a gene under one set of conditions, called permissive, but lacks that function under a different set of conditions, called nonpermissive; the latter must still be permissive for the wild-type allele of the gene. Conditional mutants are presumed, in most cases, to result from missense mutations in a structural gene encoding a protein. In the case of temperature-sensitive (ts) mutants, the amino acid replacement resulting from the missense mutation partially destabilizes the encoded protein, resulting in the maintenance of its three-dimensional integrity only at relatively low temperatures.

Conditional mutants make possible the analysis of physiological changes caused by inactivation of a gene or gene product, and can be used to address the function of any gene. This strategy is especially valuable for the analysis of essential genes. Several types of conditional mutants and methods for producing them have been developed since the original demonstration of the utility of ts mutants (Horowitz, *Genetics* 33, 612 (1948); Horowitz, *Adv. Genetics* 3, 33(1950)) but the ts phenotype is still the one most frequently used.

One limitation of the ts approach is the uncertainty as to whether a given gene can be mutated to yield a ts product. For example, only six loci were identified after repeated searches for ts lethal mutations mapping to the S. cerevisiae chromosome I, which contains at least one hundred genes (more than six of which are essential)(Kaback et al., *Genetics* 108:67 (1984); Harris and Pringle, *Genetics* 127: 279 (1991)). Another problem with conventional ts mutations is that they are often too "leaky" to be useful. That is, the function of a leaky ts protein at nonpermissive temperatures is not fully blocked by the mutation. For these and other reasons, a method for producing ts mutants which does not require a search for a ts mutation in a gene of interest would be extremely useful in a variety of applications.

SUMMARY OF THE INVENTION

The subject invention relates, in one aspect, to a heat-inducible N-degron module and to DNA encoding same. In a preferred embodiment, the DNA encoding the heat-inducible N-degron module hybridizes to the DNA represented in SEQ ID NO: 1, or its complement, under stringent hybridization conditions.

The DNA encoding the heat-inducible N-degron module can be linked covalently at its 3' end to the 5' end of a DNA sequence encoding a protein (or peptide) of interest. When expressed in a cell in which the N-end rule of protein degradation is operative, the heat-inducible N-degron module, and any protein (or peptide) linked to the C-terminus of the heat-inducible N-degron module, are rapidly degraded by enzymatic components of the N-end rule proteolytic pathway.

A specific heat-inducible N-degron module is disclosed herein. In addition, methods for the identification of additional functional heat-inducible N-degron modules are also disclosed. Such methods are useful for the isolation of heat-inducible N-degron modules using simple screening processes. Finally, it is disclosed that a low molecular weight ligand that binds to a heat-inducible N-degron can interfere with its activation by heat, thereby allowing modulation of the activity of the N-degron by agents other

Statement of Utility

Prior to the development of ts mutants, the range of genetic analysis was severely limited due to the fact that mutants which were defective in an essential function could not be studied due to the lethality of the genetic lesion. This problem was resolved, to some degree, through the development of the ts and other conditional mutants. However, the identification of a ts mutant is a laborious, time-consuming procedure which includes a first step in which mutations are randomly induced, and a second step in which mutants are isolated (e.g., by non-selective isolation, enrichment or screening, and by selective isolation procedures as well (for a review see Pringle, in *Methods in Cell Biology*, Academic Press, New York, Prescott, ed., 233–271 (1975)).

The heat-inducible N-degron module of the subject invention is useful, for example, for the generation of a ts mutant without the need for the time-consuming classical approach to identification of a ts mutant (described above). As described in detail below, the heat-inducible N-degron module is linked via its C-terminal residue to the N-terminal residue of a protein (or peptide) of interest. The protein of interest can be either essential or nonessential for cell viability. The resulting fusion protein will be rapidly degraded by the N-end rule pathway at a nonpermissive temperature, but not at a lower, permissive temperature.

DETAILED DESCRIPTION OF THE INVENTION

Figure 1:
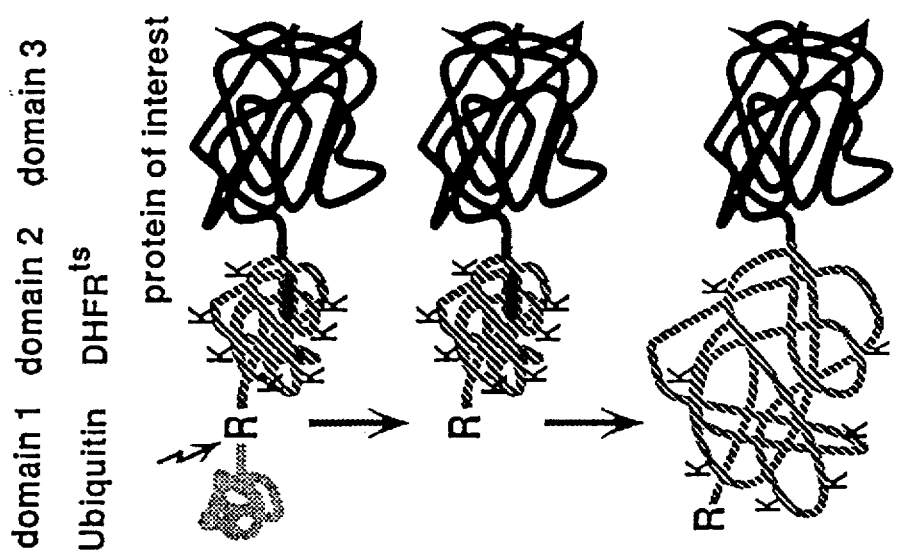
FIG. 1 is a diagram representing phenotypic characteristics of a fusion protein comprising a heat-inducible N-degron module linked at its C-terminus to the N-terminus of a protein of interest.

The N-degron is an intracellular degradation signal whose essential determinant is a specific ("destabilizing") N-terminal amino acid residue of a substrate protein. A set of N-degrons containing different destabilizing residues is manifested as the N-end rule, which relates the in vivo half-life of a protein to the identity of its N-terminal residue. The fundamental principles of the N-end rule, and the proteolytic pathway that implements it, are well-established in the literature (see, e.g., Bachmair et al., *Science* 234:179 (1986); Varshavsky, *Cell* 69:725 (1992)), and are the subject of several issued patents. Specifically, aspects of the N-end rule which are relevant to the subject invention are patented in U.S. Pat. Nos.: 5,132,213, 5,093,242 and 5,196,321, the disclosures of which are incorporated herein by reference.

In eukaryotes, the N-degron comprises at least two determinants: a destabilizing N-terminal residue and a specific internal lysine residue (or residues). The latter is the site of attachment of a multiubiquitin chain, whose formation is required for the degradation of at least some N-end rule substrates. Ubiquitin is a protein whose covalent conjugation to other proteins plays a role in a number of cellular processes, primarily through routes that involve protein degradation.

In a stochastic view of the N-degron, each internal lysine of a protein bearing a destabilizing N-terminal residue can be assigned a probability of being utilized as a multiubiquitination site, depending on time-averaged spatial location, orientation and mobility of the lysine. For some, and often for all of the Lys residues in a potential N-end rule substrate, this probability would be infinitesimal because of the lysine's lack of mobility and/or its distance from a destabilizing N-terminal residue.

The present invention is based on the discovery that it is possible to construct a thermolabile protein bearing a destabilizing N-terminal residue in such a way that the protein becomes a substrate of the N-end rule pathway only at a temperature high enough to result in at least partial unfolding of the protein. This unfolding activates a previously cryptic N-degron in the protein by increasing exposure of its (destabilizing) N-terminal residue, by increasing mobilities of its internal Lys residues, or because of both effects at once. Since proteolysis by the N-end rule pathway is highly processive, any protein of interest can be made short-lived at a high (nonpermissive) but not at a low (permissive) temperature by expressing it as a fusion to the thus engineered thermolabile protein, with the latter serving as a portable, heat-inducible N-degron module.

The heat-inducible N-degron module can be any protein or peptide bearing a destabilizing N-terminal residue which becomes a substrate of the N-end rule pathway only at a temperature high enough to be useful as a nonpermissive temperature. In the Exemplification section which follows, an example of such a heat-inducible N-degron module is provided. More specifically, the experiments described herein disclose a ts allele of the 21-kd mouse dihydrofolate reductase protein, in which the wild-type N-terminal Val is replaced by Arg.

The experimental work disclosed herein demonstrates that this ts allele functions as a heat-inducible N-degron module. More specifically, when this heat-inducible N-degron module is fused at its C-terminus to the N-terminus of a protein (or peptide) of interest, the protein (or peptide) of interest also becomes short-lived at the nonpermissive temperature due to the highly processive nature of the N-end rule pathway. Throughout this document, the use of the expression "protein of interest" specifically includes a peptide of interest. Processivity, as used in this context, is defined as the ability of a pathway to complete the initially started degradation of a protein, resulting in protein fragments whose sizes do not significantly exceed those of small peptides (e.g., less than about 20 amino acid residues). This ability is well-established for ubiquitin-dependent proteolytic pathways, and in particular for the N-end rule pathway. It is indicated in particular by the total disappearance of various protein fusions degraded by the N-end rule pathway (see e.g., Hershko, *J. Biol. Chem.* 263:15237 (1988); Rechsteiner, *Cell* 66:615 (1991); and Varshavsky, *Cell* 69, 725 (1992)).

The DNA sequence of the ts allele of the 21-kd mouse dihydrofolate reductase protein is set forth in SEQ ID NO: 1. The amino acid residues encoded by this DNA sequence are represented in SEQ ID NOS: 1 and 2. The scope of the invention encompasses any heat-inducible N-degron module which is encoded by a DNA sequence which hybridizes to the DNA sequence of SEQ ID NO: 1, or the complement thereof, under stringent hybridization conditions. Stringent hybridization conditions, as used herein, refer to hybridization in which the DNA molecule represented in SEQ ID NO: 1 is fixed to a solid support and a second DNA molecule to be tested for the ability to hybridize to the DNA of SEQ ID NO: 1 is detectably labeled and suspended in a hybridization buffer consisting essentially of 50% formamide, 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll)). The hybridization buffer is contacted with the solid support at a temperature of about 45° C. for a period of several hours. The hybridization solution is then removed, and non-specifically bound nucleic acid is removed by repeated washing with 1×SSC at increasing temperatures (up to 65° C.).

Identification of additional heat-inducible N-degron modules requires exclusively straightforward experimental procedures, such as those described in the Exemplification section, which follows. More specifically, in the experiments described below, a nucleic acid construct encoding Ub-Arg-DHFR-ha-Ura3 is described. The fusion protein encoded by this construct is carried on a plasmid which also carries a gene for a selectable marker, and has several features which facilitate the identification of a heat-inducible N-degron module. The N-terminal ubiquitin moiety is included as a transient moiety specifying a cleavage site in the encoded fusion protein between the Ub and Arg-DHFR moieties. Linear fusions of ubiquitin have been demonstrated to be efficiently cleaved between the C-terminal glycine and the N-terminal amino acid residue of the ubiquitin fusion partner (see, e.g., Bachmair et al., *Science* 234:179 (1986); Bachmair and Varshavsky, *Cell* 56:1019 (1989)). This specific cleavage is effected by a ubiquitin-specific protease activity which has been identified in all eukaryotes examined.

Arg-DHFR is a variant of the 21-kd mouse dihydrofolate reductase in which the wild-type N-terminal Val is replaced by Arg. Arg is a destabilizing residue according to the N-end rule, in that exposure of Arg at the N-terminus of a protein should, if other conditions are met as well, transform a relatively stable (long-lived) protein (such as DHFR or any other protein) to a less stable (more short-lived) protein. The "ha" portion is a 14-residue domain containing an ha epitope. The ha epitope facilitates immunoprecipitation of the Arg-DHFR-ha-Ura3 fusion with a monoclonal anti-ha antibody. The *S. cerevisiae* Ura3 domain of the fusion protein made possible selections for or against the presence of the fusion protein in cells, while also serving as a test protein.

It will be recognized that individual components of the Arg-DHFR-ha-Ura3 fusion protein can be replaced by functional homologs without compromising the value of the fusion protein for use in a method for identifying a heat-inducible N-degron module. For example, Ura 3 domain can be replaced with another selectable marker domain. Similarly, the ha epitope can be replaced by another immunological tag which facilitates immunoprecipitation of the fusion protein.

To identify additional heat-inducible N-degron modules, a modified protein or peptide moiety other than DHFR can be substituted for Arg-DHFR in the Arg-DHFR-ha-Ura3 fusion protein described above. For example, consider a protein designated "Protein X" (pX). A modified pX bearing a destabilizing N-terminal amino acid residue (e.g., Arg-pX) can be substituted for Arg-DHFR in the fusion construct described in the preceding paragraph. As described herein, this is achieved by placing the Ub moiety in front of Arg-pX within a fusion; the cotranslational cleavage of the Ub moiety at the Ub-Arg junction in vivo will then yield a protein bearing Arg-pX at its N-terminus.

The DNA encoding the Ub-Arg-pX-ha-Ura3 moiety can then be treated with a mutagen. In a ts mutant, the gene product is preferably not too dramatically altered. Therefore, it is preferable to employ mutagens characterized by a tendency to produce missense mutations rather than mutagens which tend to induce more extensive genetic lesions such as deletions. The experiments disclosed herein demonstrate that hydroxylamine is an appropriate mutagen. In addition, a variety of other known mutagens including, for example, N-methyl-N'-nitro-N-nitrosoguanidine (NG), nitrous acid (NA), ethylmethane sulfonate (EMS), and ultraviolet light are known to be useful for the generation of ts mutants (see e.g., Pringle, in *Methods in Cell Biology*, Academic Press, New York, Prescott, ed., 233–271 (1975)). The listing of appropriate mutagens provided herein is meant to provide examples of useful mutagens and is not meant to be comprehensive in the listing of useful mutagens.

The resulting DNA, carried in an appropriate plasmid, is then used to transform cells (e.g., *E. coli* MC1066 cells) to ampicillin resistance with the selection being carried out at 37° C. Transformants are then replica-plated, for example, onto M9 plates containing amp, Trp and Leu, and lacking uracil. Under this selection scheme, the yeast URA3 gene complements the Ura⁻ phenotype of *E. coli* pyrF mutants. This *E. coli* screen will eliminate mutant plasmids that do not express a functional Ura3 moiety of Ub-Arg-pX-ha-Ura3 at 37° C.

Appropriate plasmid constructs which express a functional Ura3 moiety of Ub-Arg-pX-ha-Ura3 at 37° C. are then screened for the ability to confer a ts Ura⁺ phenotype whose ts aspect requires the N-end rule pathway. This is accomplished, for example, by introducing such plasmids into *S. cerevisiae* YPH500 (ura3), with transformants selected at 23° C. on SD(-Ura) plates containing 0.1 mM CuSO$_4$. Resulting colonies are replica-plated onto plates appropriate for selection. For example, the resulting colonies can be replica-plated onto SD plates lacking His and containing 5-fluoroorotic acid (FOA) and uracil. The inclusion of FOA serves as a selection against cells expressing Ura3 (Boeke et al., *Mol. Gen. Genet.* 197, 345 (1984)). The FOA plates are then incubated at 37° C. to select against cells that could yield a functional Ura3 at 37° C. After several rounds of the FOA-mediated selection against cells that are Ura⁺ at 37° C., the ts URA⁺ phenotype of surviving cell clones can be verified by replica-plating them onto SD(-Ura, -His) plates at 37° C. Plasmids from cells passing these screens are introduced into cells such as the YPH500-derived strain JD15 (described in detail below), with transformants selected on SD(-Ura) plates at 37° C. This step narrows the selection to plasmids having the ability to confer the ts Ura⁺ phenotype only in the presence of the N-end rule pathway. Conventional sequencing techniques are then used to confirm that the mutation responsible for the desired phenotype is present within the pX domain of the fusion protein. Upon confirmation of this, the mutant Arg-pX moiety has been identified as a heat-inducible N-degron module.

DNA encoding a heat-inducible N-degron module of the type described above can be linked at its 3' end to the 5' end of DNA encoding a protein or peptide of interest, yielding a desired gene fusion construct. The gene fusion, together with any regulatory sequences required for expression, is introduced into cells using conventional techniques. The cells into which the gene fusion is introduced can be either cells grown in culture, or differentiated tissue cells in a whole organism. It will be recognized that these cells should also lack a functioning allele of the gene whose ts mutation is being sought. This can be accomplished, for example, through the use of targeted mutagenesis techniques which are well known in the art. This gene fusion construct is then expressed to produce a protein fusion in which the heat-inducible N-degron module is joined covalently at its C-terminus to the N-terminus of the protein or peptide of interest.

Provided that the cell in which the gene fusion construct is expressed is a cell in which the N-end rule degradation pathway is operative (e.g., any eukaryotic cell), the metabolic fate of the protein or peptide of interest in the fusion protein will be determined by the presence of the heat-inducible N-degron module. Due to the highly processive nature of the N-end rule degradation pathway, the recognition of a destabilizing N-terminal amino acid residue by the recognition component of the pathway seals the fate of the protein fusion. Specifically, at nonpermissive temperatures, the N-terminal residue will be recognized by the recognition component of the N-end rule degradation pathway, and the entire fusion protein will be rapidly degraded. This typically results in a strong decrease of the steady state concentration of the fusion and, consequently, in a null phenotype for the protein or peptide of interest.

Exemplification

A thermolabile protein was constructed that functions as a substrate of the N-end rule pathway only at a temperature high enough to be useful as a nonpermissive temperature. This unfolding activates a previously cryptic N-degron module in the protein. Since proteolysis by the N-end rule pathway is highly processive, any protein of interest can be made conditionally short-lived by expressing it as a fusion to the thus engineered thermolabile protein, with the latter serving as a portable, heat-inducible N-degron module.

Arg-DHFR, a variant of the 21-kd mouse dihydrofolate reductase in which the wild-type N-terminal Val is replaced by Arg, is long-lived in the yeast *S. cerevisiae* ($t_{1/2}$>6 hr at 30° C.), even though Arg (unlike Val) is a destabilizing residue in the N-end rule. A search was conducted for a ts allele of Arg-DHFR whose cryptic N-degron would be activated at 37° C. but not at 23° C. A plasmid (pPW17R) was constructed that expressed Ub-Arg-DHFR-ha-Ura3 in *S. cerevisiae*.

Briefly, referring to FIG. 1, a fusion protein on the left contains an N-terminal ubiquitin (Ub) moiety, a ts dihydrofolate reductase (DHFR$^{ts}$) moiety, with a destabilizing residue such as Arg (R) at the Ub-DHFR junction, and a test protein moiety at the C-terminus of the fusion. In the experiments described herein, the test proteins were Ura3 and Cdc28 of *S. cerevisiae*. Some of the Lys (K) residues of DHFR$^{ts}$ are indicated in FIG. 1 as well. Expression of this fusion in a eukaryote such as the yeast *S. cerevisiae* results in rapid cleavage at the Ub-DHFR junction and the exposure of a destabilizing Arg (R) residue at the N-terminus of a deubiquitinated fusion. At permissive temperature (23° C.), the N-degron module of the Arg-DHFR$^{ts}$ moiety is inactive. However, at nonpermissive temperature (37° C.), a conformational destabilization of Arg-DHFR$^{ts}$ results in at least some of its lysines becoming available as ubiquitination sites of the previously cryptic N-degron module. The processive degradation of the fusion by the N-end rule pathway then ensues, greatly reducing its level in the cell. In the examples shown, the yeast Ura3 (orotidine-5'-phosphate decarboxylase) as the C-terminal moiety of the fusion resulted in Ura⁺ cells at 23° C. but in Ura⁻ cells at 37° C. Similarly, when the essential kinase Cdc28 was expressed as an Arg-DHFR$^{ts}$-Cdc28 fusion, cells grew at 23° C, but not at 37° C. With either Arg-DHFR$^{ts}$-Ura3 or Arg-DHFR$^{ts}$-Cdc28, the absence of the N-end rule pathway (in ubr1Δ cells) precluded these conditional phenotypes at 37° C.

Thus, Arg-DHFR$^{ts}$ can be used as a portable, heat-inducible N-degron that yields ts mutants of a new class, called td (temperature-inducible degron).

More specifically, the CEN6, HIS3-based plasmid pPW17R, which expressed Ub-Arg-DHFR-ha-Ura3 from the *S. cerevisiae* $P_{CUP1}$ promoter, was constructed in the background of pRS313 (R. S. Sikorski and P. Hieter, *Genetics* 122, 19 (1989)). Briefly, a ~0.4 kb fragment from pJDC22-2 (K. Madura, R. J. Dohmen, A. Varshavsky, *J. Biol. Chem.* 268, 12046 (1993)) that contained the $P_{CUP1}$ promoter was ligated to a separately constructed fragment encoding Ub-Arg-DHFR-ha-Ura3. The DHFR moiety was followed by a 14-residue, ha epitope-containing sequence. The Ura3 moiety of Ub-Arg-DHFR-ha-Ura3 was actually a fusion of the last 91 residues of *S. cerevisiae* His4 to residue 6 of the Ura3 protein (E. Alani and N. Kleckner, *Genetics* 117, 5 (1987)).

The ubiquitin (Ub) moiety of this fusion protein was required for production of the desired residue, such as Arg, at the N-terminus of the DHFR moiety. Ubiquitin fusions are rapidly cleaved in vivo after the last residue of ubiquitin, making possible the production of otherwise identical proteins bearing different N-terminal residues (FIG. 1) (see e.g., Varshavsky, *Cell* 69, 725 (1992)). The "ha" epitope allowed immunoprecipitation of the Arg-DHFR-ha-Ura3 fusion with a monoclonal anti-ha antibody. The *S. cerevisiae* Ura3 moiety made possible selections for or against the fusion's presence in cells, while also serving as a test protein (FIG. 1).

Purified pPW17R was mutagenized with hydroxylamine (S. Busby, M. Irani, B. deCrombrugghe, *J. Mol. Biol.* 154, 197 (1982)). The resulting DNA was used to transform the Ura$^-$(pyrF) *E. coli* MC1066 (M. J. Casadaban, A. Martinez-Ariaz, S. K. Shapira, J. Chow, *Methods Enzymol.* 100, 293 (1983)) to ampicillin (amp) resistance, with selection on Luria Broth/amp plates at 37° C. Transformants were replica-plated onto M9 plates containing amp, Trp and Leu, and lacking uracil. The yeast URA3 gene complements the Ura$^-$ phenotype of *E. coli* pyrF mutants (M. Rose, P. Grisafi, D. Botstein, *Gene* 29, 113 (1984)). This *E. coli* screen eliminated mutant plasmids that did not express a functional Ura3 moiety of Ub-Arg-DHFR-ha-Ura3 at 37° C. However, those (potentially relevant) plasmids that expressed a mutant DHFR moiety were expected to pass this test since *E. coli* lacks the ubiquitin system. The N-terminal ubiquitin moiety of Ub-Arg-DHFR-ha-Ura3 was therefore retained in *E. coli*, precluding the formation of an N-degron.

A screen was carried out for derivatives of pPW17R that could confer onto Ura$^-$ cells a ts Ura$^+$ phenotype whose ts aspect required the N-end rule pathway. More specifically, plasmids that passed the *E. coli* screen described above were introduced in *S. cerevisiae* YPH500 (ura3), (R. S. Sikorski and P. Hieter, *Genetics* 122, 19 (1989)), with transformants selected at 23° C. on SD(-Ura) plates containing 0.1 mM CuSO$_4$. The colonies were replica-plated onto SD plates lacking His and containing 5-fluoroorotic acid (FOA) and uracil (J. D. Boeke, F. Lacroute, G. R. Fink, *Mol. Gen. Genet.* 197, 345 (1984)). The FOA plates were incubated at 37° C. to select against cells (carrying pPW17R plasmids) that could yield a functional Ura3 at 37° C. After several rounds of the FOA-mediated selection against cells that were Ura$^+$ at 37° C., the ts URA$^+$ phenotype of surviving cell clones was verified by replica-plating them onto SD(-Ura, -His) plates at 37° C. Plasmids from cells that passed these screens were introduced into the YPH500-derived strain JD15 (ubr1-Δ1::LEU2 ura3, produced identically to ubr1Δ strains described previously (B. Bartel, I. Wunning, A. Varshavsky, *EMBO J.* 9, 3179 (1990); K. Madura, R. J. Dohmen, A. Varshavsky, *J. Biol. Chem.* 268, 12046 (1993)), with transformants selected on SD(-Ura) plates at 37° C. This step narrowed the selection to plasmids whose ability to confer the ts Ura$^+$ phenotype required the presence of the N-end rule pathway.

This screen yielded two mutant plasmids with the desired properties: at 23° C., these plasmids conferred a Ura$^+$ phenotype, whereas at 37° C. they conferred a Ura$^-$ phenotype in [UBR1 ura3] cells but a Ura$^+$ phenotype in congenic [ubr1Δ ura3] cells. The [ubr1Δ ura3] strain lacked the N-end rule pathway because it lacked N-recognin (encoded by UBR1), the recognition component of the degradation pathway. The relevant change in both plasmids was a single missense mutation that replaced Pro with Leu at position 66 in the DHFR moiety of Ub-Arg-DHFR-ha-Ura3, yielding Ub-Arg-DHFR$^{ts}$-ha-Ura3. The Pro$^{66}$ region of DHFR connects its αII helix to the βC strand (C. Oefner, A. D'Arcy, F. K. Winkler, *Eur. J. Biochem.* 174, 377 (1988); K. W. Volz et al., *J. Biol. Chem.* 257, 2528 (1982)). The final construct, termed pPW43R, was produced from the unmutagenized pPW17R by replacing its EcoRI fragment encoding Ub-Arg-DHFR-ha-Ura3 with the otherwise identical fragment from one of the above plasmids encoding Ub-Arg-DHFR$^{ts}$-ha-Ura3.

Arg-DHFR$^{ts}$ was then used to produce a ts version of the *S. cerevisiae* Cdc28 protein kinase—an essential component of the cell cycle oscillator. The chromosomal CDC28 gene was replaced with a gene that expressed Ub-Arg-DHFR$^{ts}$-ha-Cdc28. More specifically, the plasmid pPW66R was constructed in the background of the integration vector pRS306, (R. S. Sikorski and P. Hieter, *Genetics* 122, 19 (1989)). Briefly, the previously described DNA fragment encoding Ub-Arg-DHFR$^{ts}$-ha was ligated to a fragment (produced using PCR and *S. cerevisiae* genomic DNA) that encompassed the first 284 nucleotides of the CDC28 ORF (S. I. Reed, *Annu. Rev. Cell Biol.* 8, 529 (1992); A. Murray, *Nature* 359, 599 (1992); A. B. Futcher, *Semi. Cell Biol.* 2, 205 (1991); K. Nasmyth, L. Dirick, U. Surana, A. Amon, F. Cvrckova, *Cold Spring Harbor Symp. Quant. Biol.* 56, 9 (1991); P. Nurse, *Nature* 344, 503 (1990)). The resulting fragment, encoding Ub-Arg-DHFR$^{ts}$-ha-Cdc28$_{1-95}$, was positioned downstream from the $P_{CUP1}$ promoter in pRS306, yielding pPW66R. This plasmid was linearized at the Msc I site (nucleotide 92 in the CDC28 ORF) and transformed into *S. cerevisiae* YPH500. In the resulting Ura$^+$ integrants, homologous recombinations (R. Rothstein, *Methods Enzymol.* 194, 281 (1991)) between the proximal regions of CDC28 in pPW66R and in Chromosome II resulted in the integration of pPW66R and formation of an ORF encoding Ub-Arg-DHFR$^{ts}$-ha-Cdc28 (which contained the full-length CDC28$_{1-299}$ moiety), in addition to a nearby sequence encoding Cdc28$_{1-95}$. This truncated allele of CDC28 was neither functional nor dominant negative.

The resulting *S. cerevisiae* strains were compared to the wild-type (CDC28) strain YPH500. Whereas the wild-type strain grew at both 23° C. and 37° C., a representative strain expressing Ub-Arg-DHFR$^{ts}$-ha-Cdc28 (instead of the wild-type Cdc28) grew at 23° C. but was inviable at 37° C. The morphology of these cells was examined following the temperature upshift in liquid culture. After 2 hr at 37° C., cells that expressed Ub-Arg-DHFR$^{ts}$-ha-Cdc28 became larger but lacked buds (G1 phase morphology); however, by 4 hr at 37° C., many of these cells developed abnormal (elongated) buds and arrested in this configuration, which is similar to the arrest phenotype observed with some of the conventional ts alleles of CDC28. This Cdc28-mediated ts lethal phenotype required the presence of the N-end rule pathway, inasmuch as ubr1Δ cells that expressed Ub-Arg-DHFR$^{ts}$-ha-Cdc28 grew at both 23° C. and 37° C., and remained morphologically normal at 37° C.

Pulse-chase experiments confirmed that Arg-DHFR$^{ts}$-ha-Cdc28 was long-lived at 23° C. but short-lived at 27° C. ($t_{1/2}$<10 min). More specifically, exponential cultures of either UBR1 or ubr1Δ S. cerevisiae that expressed Arg-DHFR$^{ts}$-ha-Cdc28$^{ts}$, were labeled with $^{35}$S-methionine for 5 min at 23° C., followed by a chase at 23° C. or 37° C. for zero, 10 and 30 min, extraction, immununoprecipitation with anti-ha antibody, and SDS-PAGE analysis. The onset of metabolic instability of Arg-DHFR$^{ts}$-ha-Cdc28 upon the temperature upshift was extremely rapid. As could be expected from the results of phenotypic analysis, Arg-DHFR$^{ts}$-ha-Cdc28 was long-lived at both temperatures in ubr1Δ cells which lacked the N-end rule pathway.

In addition, it was found that the addition of a specific DHFR ligand, methotrexate (MTX), to cells whose essential Cdc28 protein is expressed as the ts degron-bearing fusion (Ub-Arg-DHFR$^{ts}$-ha-Cdc28) resulted in the inhibition of heat induction of the ts N-degron upon transfer of cells to nonpermissive (N-degron-inducing) temperature.

Specifically, cells expressing Ub-Arg-DHFR$^{ts}$-ha-Cdc28 remained viable at 37° C. in the presence of MTX at a sufficiently high concentration in the medium, whereas in the absence of MTX at 37° C. these cells ceased division and died, as described above. Pulse-chase experiments confirmed that this viability-rescuing effect of MTX (which is known to bind DHFR tightly and specifically) was due to the inhibition of degradation of Ub-Arg-DHFR$^{ts}$-ha-Cdc28 at 37° C. as a result of binding of MTX to DHFR.

This discovery indicated that the activity of an N-degron can also be modulated by agents other than temperature, making possible new classes of conditional mutants. Specifically, these results identified MTX as an agent that inhibits the activity of the N-degron based on the MTX ligand DHFR. They also pointed out the way to identify other such agents for N-degrons other than those based on DHFR. Specifically, these results indicated that the binding of a low molecular weight ligand to a protein component of an N-degron can interfere with the unfolding of this protein module at nonpermissive temperatures, and thereby can interfere with the targeting of the said degron by the corresponding proteolytic pathway such as the N-end rule pathway.

We claim:

1. A heat-inducible N-degron module comprising:
   a) a destabilizing N-terminal amino acid residue;
   b) an internal lysine amino acid residue which functions as an attachment site for a multiubiquitin chain at a permissive temperature, but not at a non-permissive temperature in a eukaryotic cell or cell extract; the heat-inducible N-degron module being encoded by a DNA sequence which hybridizes, under stringent hybridization conditions, to the DNA sequence represented in SEQ ID NO: 1.

2. The heat-inducible N-degron module of claim 1 wherein the DNA sequence encodes a variant of wild-type mouse DHFR in which the amino acid residue corresponding to proline at position 66 of wild-type mouse DHFR is replaced with a non-proline residue.

3. The heat-inducible N-degron module of claim 2 wherein the non-proline residue is leucine.

4. A fusion protein comprising a heat-inducible N-degron module, the heat-inducible N-degron module comprising:

a) a destabilizing N-terminal amino acid residue;

b) an internal lysine amino acid residue which functions as an attachment site for a multiubiquitin chain at a permissive temperature, but not at a non-permissive temperature in a eukaryotic cell or cell extract;

the heat inducible N-degron module being joined covalently at its C-terminus to the N-terminus of a protein of interest, the heat inducible N-degron module being encoded by a DNA sequence which hybridizes, under stringent hybridization conditions, to the DNA sequence represented in SEQ ID NO: 1.

5. The fusion protein of claim 4 wherein the DNA sequence encodes a variant of wild-type mouse DHFR in which the amino acid residue corresponding to proline at position 66 of wild-type mouse DHFR is replaced with a non-proline residue.

6. The fusion protein of claim 5 wherein the non-proline residue is leucine.

7. A cell containing a fusion protein comprising a heat-inducible N-degron module, the heat-inducible N-degron module comprising:

a) a destabilizing N-terminal amino acid residue;

b) an internal lysine amino acid residue which functions as an attachment site for a multiubiquitin chain at a permissive temperature, but not at a non-permissive temperature in a eukaryotic cell or cell extract;

the heat-inducible N-degron module being joined covalently at its C-terminus to the N-terminus of a protein of interest, the heat inducible N-degron module being encoded by a DNA sequence which hybridizes, under stringent hybridization conditions, to the DNA sequence represented in SEQ ID NO: 1.

8. The cell of claim 7 wherein the DNA sequence encodes a variant of wild-type mouse DHFR in which the amino acid residue corresponding to proline at position 66 of wild-type mouse DHFR is replaced with a non-proline residue.

9. The cell of claim 8 wherein the non-proline residue is leucine.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 579 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..579

( x i ) SEQUENCE DESCRIPTION: SEQ ID NO:1:

```
AGG  CAC  GGA  TCC  GGC  ATC  ATG  GTT  CGA  CCA  TTG  AAC  TGC  ATC  GTC  GCC        48
Arg  His  Gly  Ser  Gly  Ile  Met  Val  Arg  Pro  Leu  Asn  Cys  Ile  Val  Ala
 1                    5                        10                       15

GTG  TCC  CAA  AAT  ATG  GGG  ATT  GGC  AAG  AAC  GGA  GAC  CTA  CCC  TGG  CCT        96
Val  Ser  Gln  Asn  Met  Gly  Ile  Gly  Lys  Asn  Gly  Asp  Leu  Pro  Trp  Pro
                      20                       25                       30

CCG  CTC  AGG  AAC  GAG  TTC  AAG  TAC  TTC  CAA  AGA  ATG  ACC  ACA  ACC  TCT       144
Pro  Leu  Arg  Asn  Glu  Phe  Lys  Tyr  Phe  Gln  Arg  Met  Thr  Thr  Thr  Ser
           35                       40                       45

TCA  GAG  GAA  GGT  AAA  CAG  AAT  CTG  GTG  ATT  ATG  GGT  AGG  AAA  ACC  TGG       192
Ser  Glu  Glu  Gly  Lys  Gln  Asn  Leu  Val  Ile  Met  Gly  Arg  Lys  Thr  Trp
      50                       55                       60

TTC  TCC  ATT  CCT  GAG  AAG  AAT  CGA  CTT  TTA  AAG  GAC  AGA  ATT  AAT  ATA       240
Phe  Ser  Ile  Pro  Glu  Lys  Asn  Arg  Leu  Leu  Lys  Asp  Arg  Ile  Asn  Ile
 65                      70                       75                       80

GTT  CTC  AGT  AGA  GAA  CTC  AAA  GAA  CCA  CCA  CGA  GGA  GCT  CAT  TTT  CTT       288
Val  Leu  Ser  Arg  Glu  Leu  Lys  Glu  Pro  Pro  Arg  Gly  Ala  His  Phe  Leu
                      85                       90                       95

GCC  AAA  AGT  TTG  GAT  GAT  GCC  TTA  AGA  CTT  ATT  GAA  CAA  CCG  GAA  TTG       336
Ala  Lys  Ser  Leu  Asp  Asp  Ala  Leu  Arg  Leu  Ile  Glu  Gln  Pro  Glu  Leu
```

```
              100                    105                       110
    GCA AGT AAA GTA GAC ATG GTT TGG ATA GTC GGA GGC AGT TCT GTT TAC    384
    Ala Ser Lys Val Asp Met Val Trp Ile Val Gly Gly Ser Ser Val Tyr
            115             120                 125

CAG GAA GCC ATG AAT CAA CCA GGC CAC CTC AGA CTC TTT GTG ACA AGG    432
    Gln Glu Ala Met Asn Gln Pro Gly His Leu Arg Leu Phe Val Thr Arg
        130             135                 140

ATC ATG CAG GAA TTT GAA AGT GAC ACG TTT TTC CCA GAA ATT GAT TTG    480
    Ile Met Gln Glu Phe Glu Ser Asp Thr Phe Phe Pro Glu Ile Asp Leu
    145             150                 155                     160

GGG AAA TAT AAA CTT CTC CCA GAA TAC CCA GGC GTC CTC TCT GAG GTC    528
    Gly Lys Tyr Lys Leu Leu Pro Glu Tyr Pro Gly Val Leu Ser Glu Val
                    165             170                 175

CAG GAG GAA AAA GGC ATC AAG TAT AAG TTT GAA GTC TAC GAG AAG AAA    576
    Gln Glu Glu Lys Gly Ile Lys Tyr Lys Phe Glu Val Tyr Glu Lys Lys
                180             185                 190

GAC                                                                579
    Asp
```

( 2 ) INFORMATION FOR SEQ ID NO:2:

( i ) SEQUENCE CHARACTERISTICS:
        ( A ) LENGTH: 193 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Arg His Gly Ser Gly Ile Met Val Arg Pro Leu Asn Cys Ile Val Ala
 1               5                  10                  15

Val Ser Gln Asn Met Gly Ile Gly Lys Asn Gly Asp Leu Pro Trp Pro
                20                  25                  30

Pro Leu Arg Asn Glu Phe Lys Tyr Phe Gln Arg Met Thr Thr Thr Ser
            35                  40                  45

Ser Glu Glu Gly Lys Gln Asn Leu Val Ile Met Gly Arg Lys Thr Trp
    50                  55                  60

Phe Ser Ile Pro Glu Lys Asn Arg Leu Leu Lys Asp Arg Ile Asn Ile
65                  70                  75                  80

Val Leu Ser Arg Glu Leu Lys Glu Pro Pro Arg Gly Ala His Phe Leu
                85                  90                  95

Ala Lys Ser Leu Asp Asp Ala Leu Arg Leu Ile Glu Gln Pro Glu Leu
            100                 105                 110

Ala Ser Lys Val Asp Met Val Trp Ile Val Gly Gly Ser Ser Val Tyr
        115                 120                 125

Gln Glu Ala Met Asn Gln Pro Gly His Leu Arg Leu Phe Val Thr Arg
    130                 135                 140

Ile Met Gln Glu Phe Glu Ser Asp Thr Phe Phe Pro Glu Ile Asp Leu
145                 150                 155                 160

Gly Lys Tyr Lys Leu Leu Pro Glu Tyr Pro Gly Val Leu Ser Glu Val
                165                 170                 175

Gln Glu Glu Lys Gly Ile Lys Tyr Lys Phe Glu Val Tyr Glu Lys Lys
            180                 185                 190

Asp
```